United States Patent
Hess et al.

(10) Patent No.: US 9,545,328 B2
(45) Date of Patent: Jan. 17, 2017

(54) PATELLAR PAD

(75) Inventors: Heinrich Hess, Kleinblittersdorf (DE); Rainer Scheuermann, Raisdorf (DE); Hans B. Bauerfeind, Zeulenroda-Triebes (DE); Oliver Marx, Zwickau (DE)

(73) Assignee: BAUERFEIND AG (DE)

( * ) Notice: Subject to any disclaimer, the term of this patent is extended or adjusted under 35 U.S.C. 154(b) by 193 days.

(21) Appl. No.: 13/981,629

(22) PCT Filed: Jan. 25, 2012

(86) PCT No.: PCT/EP2012/000338
§ 371 (c)(1),
(2), (4) Date: Sep. 5, 2013

(87) PCT Pub. No.: WO2012/104037
PCT Pub. Date: Aug. 9, 2012

(65) Prior Publication Data
US 2013/0338557 A1    Dec. 19, 2013

(30) Foreign Application Priority Data

Jan. 31, 2011 (DE) .................. 10 2011 010 827

(51) Int. Cl.
*A61F 5/01* (2006.01)
*A61F 5/30* (2006.01)
*A61F 13/06* (2006.01)

(52) U.S. Cl.
CPC .............. *A61F 5/0125* (2013.01); *A61F 5/30* (2013.01); *A61F 13/061* (2013.01); *A61F 2005/0176* (2013.01); *Y10T 29/49826* (2015.01)

(58) Field of Classification Search
CPC combination set(s) only.
See application file for complete search history.

(56) References Cited

U.S. PATENT DOCUMENTS

| | | | | |
|---|---|---|---|---|
| 4,201,203 A | * | 5/1980 | Applegate | A61F 5/0109 2/24 |
| 6,149,616 A | * | 11/2000 | Szlema | A61F 13/061 602/26 |
| 6,540,711 B2 | * | 4/2003 | Cox | A61F 5/0106 128/116.1 |

FOREIGN PATENT DOCUMENTS

| | | |
|---|---|---|
| DE | 36 37 879 A1 | 5/1988 |
| DE | 93 00 600 U1 | 3/1993 |
| DE | 298 03 103 U1 | 5/1998 |

OTHER PUBLICATIONS

English language translation of International Preliminary Report on Patentability issued in corresponding International Application No. PCT/EP2012/000338.
International Search Report dated Mar. 27, 2012 issued in corresponding International patent application PCT/EP2012/000338.
International Preliminary Report on Patentability dated Apr. 22, 2013 issued in corresponding International patent application PCT/EP2012/000338.

* cited by examiner

*Primary Examiner* — Ophelia A Hawthorne
(74) *Attorney, Agent, or Firm* — Ostrolenk Faber LLP

(57) ABSTRACT

A medical aid for supporting the function of the knee joint, in particular a knee joint orthosis with a pad engaging around the patella of the knee joint. An improved patellar pad has the additional function of supporting movement and has additional preventive/therapeutic functions.

10 Claims, 2 Drawing Sheets

PATELLAR PAD

CROSS-REFERENCE TO RELATED APPLICATIONS

The present application is a 35 U.S.C. §§371 national phase conversion of PCT/EP2012/000338, filed Jan. 25, 2012, which claims priority of German Application No. 10 2011 010 827.0, filed Jan. 31, 2011, the contents of which are incorporated by reference herein. The PCT International Application was published in the German language.

BACKGROUND OF THE INVENTION

The invention relates to medical aids for supporting the function of the knee joint, in particular to knee-joint orthoses with a pad engaging around the patella of the knee joint. The invention makes available an improved patellar pad which has the additional function of supporting movement and has additional preventive/therapeutic functions.

Knee-joint orthoses are known with an annular or semi-annular pad cushion that encloses the patella of the knee joint when the orthosis is fitted in place. As is known, such orthoses can be designed as stocking-like or hose-like elastic knits. In the area of the patella, a pad is fitted in the knit. The pad supports the patella and fixes the latter in the physiologically correct position in the joint, in particular in conjunction with the pressure conferred by the elastic knit. Known pads are made from an elastic material such as silicone rubber or polyurethane or similar materials.

Below the knee joint, particularly in the anterior compartment of the knee, an infrapatellar fat body, or Hoffa's fat pad, lies to both sides of the knee cap. Under certain physiological and hormonal conditions, hyperplasia of the fat body takes place and, in some cases, hypotrophy with permanent replacement of the fat cells by collagenous connective tissue. When bending and extending the knee in such cases, there is a significant increase in pressure in the fat body, which is associated with painful and restricted movement. In the healthy organism, the infrapatellar fat body serves to support the joint function by primarily filling volumes in the joint interstices, in order to ensure a completely congruent closure in every movement state between the joint elements of tibia, femur and patella, particularly the femoral condyles, the anterior horns of the meniscus, and the tibial plateau. The infrapatellar fat body is also ascribed the role of soft-tissue embedding of tendons, particularly the patellar tendon, for stabilizing the patella in the extension position, and of mechanically damping the load transfer and positioning the patella. Certain conditions can involve a reduction in volume and atrophy of the fat bodies. The supporting function is then no longer ensured. In addition, the infrapatellar fat bodies are also directly implicated in the development of pain in the knee joint. Tests show that the fat bodies themselves are innervated with pressure sensors and pain-conducting fibers.

The object of the invention is to extend the field of use of knee-joint bandages and orthoses of the type in question, with an inserted patellar pad, such that pathological states connected with the infrapatellar fat body of the knee joint, in particular pain and restricted movements, can be treated preventively and therapeutically.

SUMMARY OF THE INVENTION

The technical problem addressed by the invention is solved by the provision of a new design of pad for a knee-joint orthosis. This pad has an annular or semi-annular base known per se which, in the fitted state of the orthosis or bandage, can engage around or enclose the patella. According to the invention, projections are formed distally on this base, particularly in pairs, and face the joint. They are designed in such a way that, in the fitted state of the orthosis or bandage, they can each be located in the area of the infrapatellar fat bodies of the knee joint and can thus each exert pressure on these. The projections are designed in particular as knobs or fingers that protrude or issue from the pad ring or pad arch.

In a preferred design, the distal projections force the distal fatty tissue upward in particular, such that the projections are preferably able, according to the invention, to slide at least partially under the inferior patellar pole and stabilize the latter. The patella is thus able to lift away from the bones of the knee joint, and a rubbing connection and associated further wear and pain are alleviated or prevented.

The pad, in terms of its basic shape (pad base), is in particular annular and encloses the patella. In another particular embodiment, the pad is horseshoe-shaped, that is to say semi-annular, and engages at least distally around the patella.

In a manner known per se, the new type of pad is preferably inserted into an elastic knitted orthosis. The pad is pressed by the knitted orthosis onto the knee joint in the area of the patella. The distal projections exert their effect mainly in conjunction with the elastic base knit of the bandage and interact therewith as a result of the movement.

In a preferred embodiment, the pad additionally has lateral projections arranged distally on its base. These lateral projections are designed in such a way that, in the fitted state of the orthosis or bandage, they can engage in lateral joint spaces located distally from the patella.

In particular, the combination of the projections that can be located in the area of the infrapatellar fat body and of the distal, lateral projections surprisingly affords a suitable physico-mechanical effect on the infrapatellar joint apparatus, especially of the infrapatellar fat body, by the new kind of pad. The inventors found to their surprise that, as a result of the pressure imparted by these projections of the pad according to the invention and applied to the infrapatellar joint apparatus, especially to the infrapatellar fat body, the anterior knee pain syndrome known per se can be treated specifically, the function of the fat body in supporting the function of the joint can be improved, and edema or hyperplasia or hypertrophy of the fat bodies can be treated preventively and therapeutically.

In addition, provision is also preferably made that the distal projections according to the invention directed toward the joint thus come into engagement with the anatomical structures thereof and thus support the exact anatomical positioning of the bandage.

The distal projections of the pad according to the invention also permit better positioning of the pad over the patella. The projections as it were "lock" into the distal depressions of the knee-joint space and stabilize the position of the pad on the patella and thus secure the action of the joint bandage.

The pad is preferably made of a permanently elastic material, in particular silicone rubber or polyurethane. However, the invention is not limited to these materials. A person skilled in the art is equally familiar with suitable materials. In this connection, the physico-mechanical behavior of the material, especially the modulus of elasticity, is in particular adapted to the soft tissue of the knee joint.

In a particular embodiment of the invention, the height and/or the resiliency of the distal projections of the pad directed toward the fat body can be individually configured in order to individually control the pressure on the fat bodies. This may be desirable in the context of a therapy plan or for achieving various preventive or therapeutic goals. To this end, the invention proposes, for example, that the pad according to the invention is connected releasably to the knee-joint orthosis or bandage and can be removed therefrom for the purpose of adjusting or adapting the height or the material properties of the projections, especially the resiliency, i.e. Shore hardness, and can then be re-inserted. Provision is made in particular that the distal projections on the pad base are exchangeable for the purpose of adjusting the effect of the pad on the fat body, especially that projections with other heights or with other mechanical properties can be used. Alternatively, provision can be made that the whole pad, base and projections, is designed as an integral one-piece element and, in order to adjust the effect on the fat body, can be replaced in its entirety by a pad with other mechanical properties, especially material properties.

The invention also relates to a knee-joint orthosis or knee-joint bandage containing the pad according to the invention. It is designed in particular as a knitted orthosis with an inserted pad according to the invention.

The invention also relates to the use of the pad according to the invention, with the projections formed thereon, for improving and/or securing the positioning of the joint orthosis on the joint of the body.

The invention also relates to the therapeutic and/or preventive use of the pad according to the invention in a knee-joint orthosis for supporting the congruent closure between the infrapatellar joint elements. The invention also relates to the preventive and/or therapeutic use of the pad according to the invention in a knee-joint orthosis for supporting the biomechanical function of the infrapatellar fat body of the knee joint, i.e. in particular the function thereof in supporting the joint.

The invention also relates to the preventive and/or therapeutic use of the pad according to the invention in a knee-joint orthosis for stabilizing the patella of the knee joint in the extension position.

The invention also relates to the preventive and/or therapeutic use of the pad according to the invention in a knee-joint orthosis for treatment of anterior knee pain syndrome.

Finally, the invention further relates to the preventive and/or therapeutic use of the pad according to the invention in a knee-joint orthosis for treatment of edema formation in the infrapatellar fat bodies of the knee joint.

The invention is described in more detail with reference to the following figures. The embodiments of the invention that are shown there are not to be understood as limiting the invention.

DESCRIPTION OF EMBODIMENTS

Figure 1:
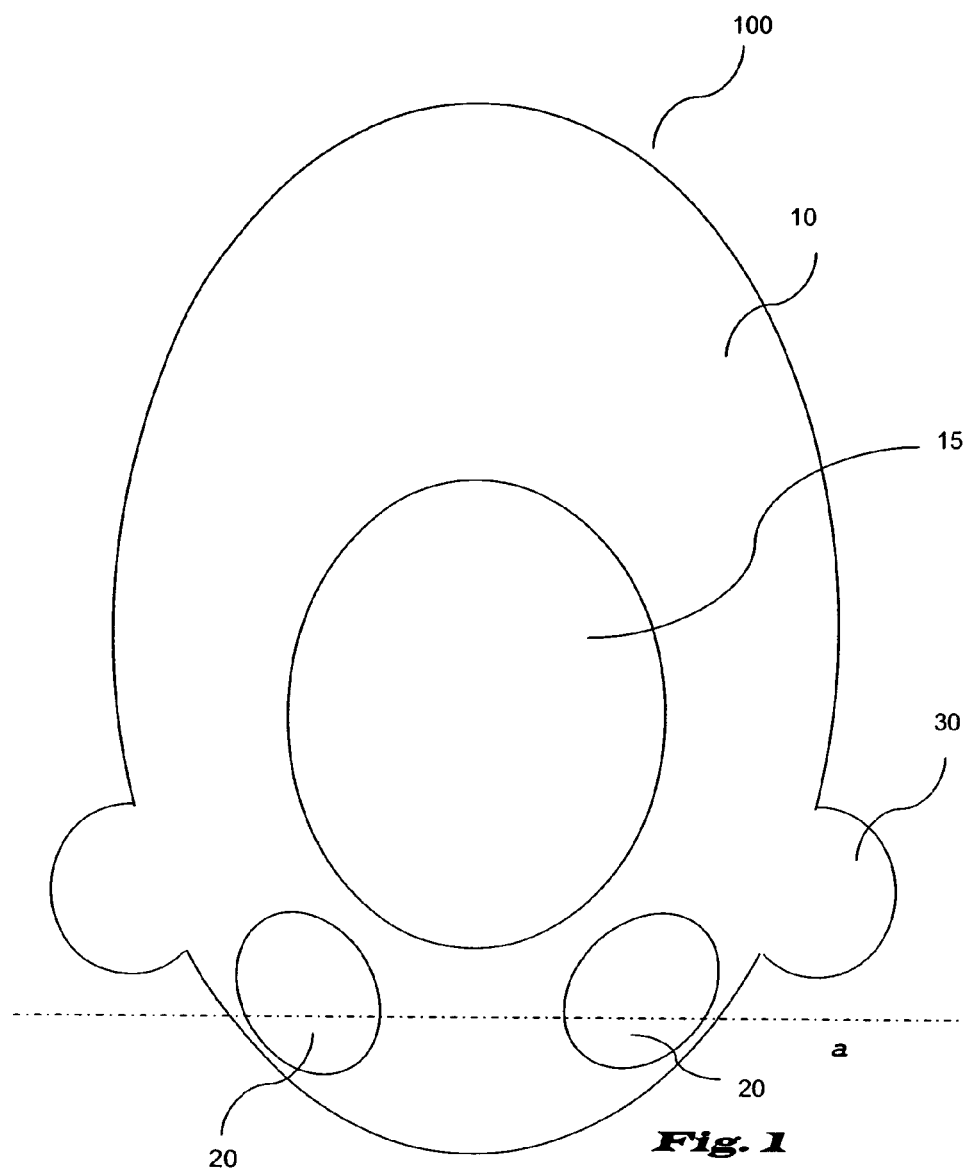
FIG. 1 is a plain view of a pad according to the invention.

FIG. 1 shows a design of the pad (100) according to the invention with an annular base (10), which encloses the patella located in the recess (15). According to the invention, the base (10) has a pair of knob-like projections (20) facing toward the joint. The pad additionally has distal, lateral wing-shaped projections (30).

Figure 2:
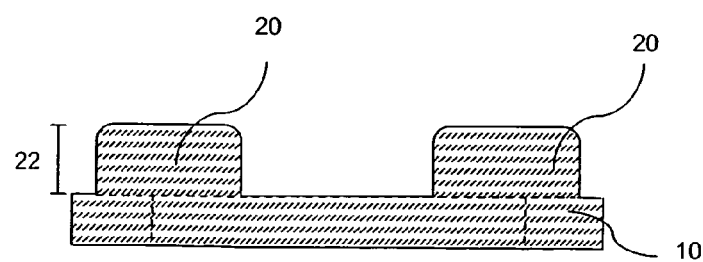
FIG. 2 is a cross-sectional view on line a in FIG. 1.

FIG. 2 shows a cross section on the sectional line a (FIG. 1). The knob-like projections (20) protrude from the base (10) in the direction of the joint by a predeterminable height (22).

Figure 3:
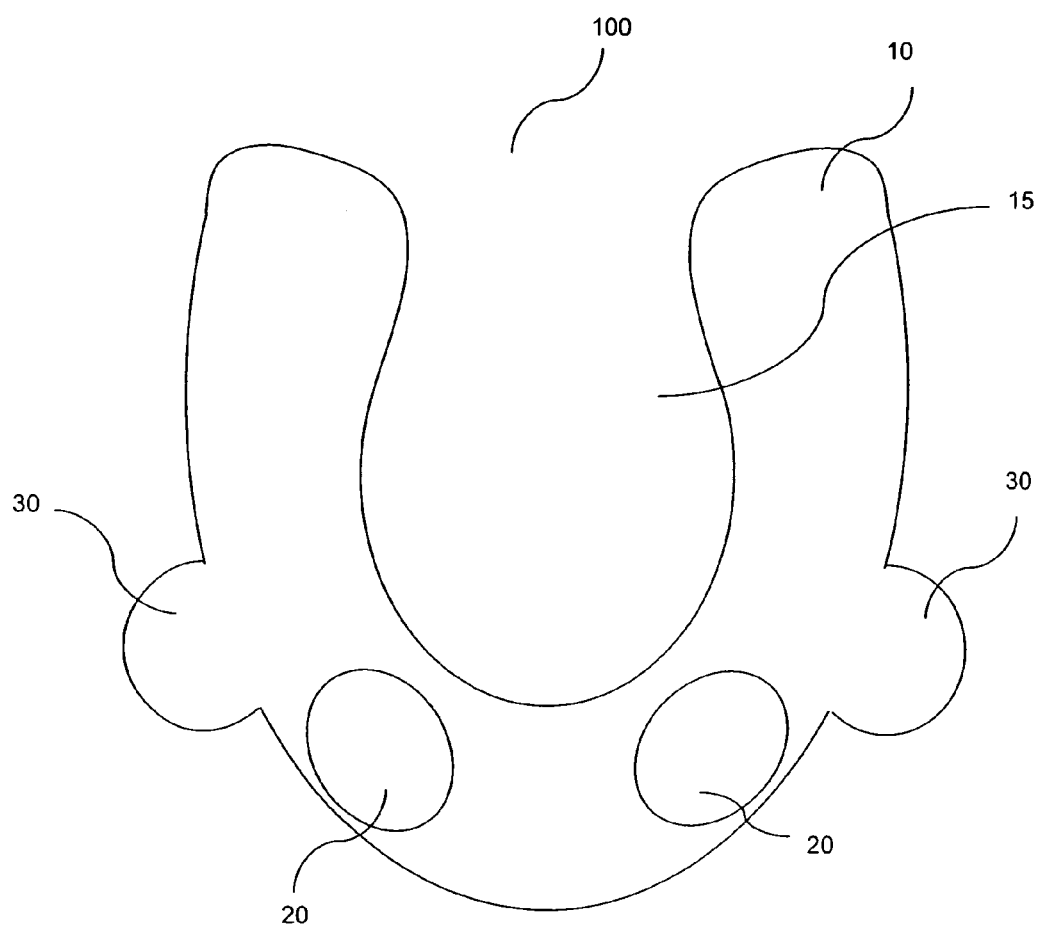
FIG. 3 shows an alternative pad design.

FIG. 3 shows an alternative design of the pad (100) which engages distally, in a semicircular or horseshoe shape, around the patella located in the recess (15).

The invention claimed is:

1. A pad for a knee joint orthosis, said pad having an annular base configured for engaging around a patella of a subject to which said pad is applied, wherein a pair of projections configured to face a knee joint of said subject are formed distally on the base and which, in a fitted state of the pad, are configured to be located in an area of infrapatellar fat bodies of said subject and are adapted to exert pressure on said fat bodies, and wherein the base additionally has lateral wing-shaped projections which, in the fitted state of the pad, are configured to come into engagement with the infrapatellar joint spaces of said subject.

2. The pad according to claim 1, wherein the projections adapted to act on the fat bodies are adjustable in terms of their mechanical properties or are exchangeable.

3. A method for applying the pad according to claim 1, wherein the method comprises:
applying the pad to a knee-joint orthosis of said subject, wherein the orthosis is configured for improving and/or securing positioning of the knee-joint orthosis on the subject's knee joint.

4. A method for applying the pad according to claim 1, comprising:
applying the pad to a knee-joint orthosis of said subject, wherein the orthosis is configured for preventive or therapeutic support of a congruent closure between infrapatellar joint elements of said subject.

5. A method for applying a pad according to claim 1, comprising:
applying the pad to a knee-joint orthosis of said subject, wherein the orthosis is configured for preventive or therapeutic support of biomechanical function of an infrapatellar fat body of the knee joint of said subject.

6. A method for applying a pad according to claim 1, comprising:
applying the pad to a knee-joint orthosis of said subject, wherein the orthosis is configured for preventive or therapeutic stabilization of the patella of the knee joint of said subject in an extension position.

7. A method for applying a pad according to claim 1, comprising:
applying the pad to a knee-joint orthosis of said subject, wherein the orthosis is configured for prevention or therapy of anterior knee pain syndrome in said subject.

8. A method for applying a pad according to claim 1, comprising:
applying the pad to a knee-joint orthosis of said subject, wherein the orthosis is configured for prevention or therapy of edema formation in the infrapatellar fat bodies of the knee joint of said subject.

9. A knee joint orthosis containing the pad according to claim 1.

10. A knee joint orthosis according to claim 9, which is an elastic knitted orthosis.

* * * * *